(12) United States Patent
Lee et al.

(10) Patent No.: US 11,524,021 B2
(45) Date of Patent: Dec. 13, 2022

(54) USE OF GINSENOSIDE M1 FOR MANUFACTURING MEDICAMENT FOR TREATING ORAL CANCER

(71) Applicant: Sheau-Long Lee, Taoyuan (TW)

(72) Inventors: Sheau-Long Lee, Taoyuan (TW); Kuo-Feng Hua, I-Lan (TW); Yu-Chieh Lee, Taoyuan (TW)

(73) Assignee: Sheau-Long Lee, Taoyuan (TW)

( * ) Notice: Subject to any disclaimer, the term of this patent is extended or adjusted under 35 U.S.C. 154(b) by 0 days.

(21) Appl. No.: 16/958,902

(22) PCT Filed: Apr. 17, 2019

(86) PCT No.: PCT/CN2019/083058
§ 371 (c)(1),
(2) Date: Jun. 29, 2020

(87) PCT Pub. No.: WO2019/201280
PCT Pub. Date: Oct. 24, 2019

(65) Prior Publication Data
US 2021/0023104 A1    Jan. 28, 2021

Related U.S. Application Data

(60) Provisional application No. 62/658,732, filed on Apr. 17, 2018.

(51) Int. Cl.
*A61K 31/704*    (2006.01)
*A61P 35/00*    (2006.01)

(52) U.S. Cl.
CPC ............ *A61K 31/704* (2013.01); *A61P 35/00* (2018.01)

(58) Field of Classification Search
CPC ...... A61K 36/258; A61K 31/704; A61P 35/00
See application file for complete search history.

(56) References Cited

U.S. PATENT DOCUMENTS 9,844,560 B2* 12/2017 Lee .................. A61P 37/00
2003/0185910 A1* 10/2003 Yun .................. A61K 36/258
424/728

OTHER PUBLICATIONS

Shen (Chinese Medicine; 2013, 8:22, pp. 1-11).*

* cited by examiner

*Primary Examiner* — Pancham Bakshi
(74) *Attorney, Agent, or Firm* — Birch, Stewart, Kolasch & Birch, LLP

(57) ABSTRACT

A use of ginsenoside M1 for manufacturing a medicament for treating oral cancer.

5 Claims, 11 Drawing Sheets

USE OF GINSENOSIDE M1 FOR MANUFACTURING MEDICAMENT FOR TREATING ORAL CANCER

CROSS REFERENCE TO RELATED APPLICATIONS

This application is the National Phase of PCT International Application No. PCT/CN2019/083058, filed on Apr. 17, 2019, which claims priority under 35 U.S.C. 119(e) to U.S. Provisional Application No. 62/658,732, filed on Apr. 17, 2018, all of which are hereby expressly incorporated by reference into the present application.

FIELD OF THE INVENTION

The present invention relates to a new use of ginsenoside M1 for treating oral cancer, particularly oral squamous cell carcinoma (OSCC).

BACKGROUND OF THE INVENTION

According to the recent report from the Department of Health, Executive Yuan, Taiwan, oral cancer affects a significant number of patients in their economically productive age and approximately 2300 men in Taiwan with an average age of 58.3 years succumb to oral cancer every year. Oral cancer is also a common malignancy worldwide and the incidence of oral cancer continues to increase annually (Murugan et al., 2012). The usual therapy for oral cancer involves one or more of the following modalities: surgery, chemotherapy and radiotherapy. Unfortunately, despite advances in clinical management, the survival rate remains poor (Petti and Scully, 2007; Tsantoulis et al., 2007). Further, some anti-cancer treatments have toxic side effects (for example, toxic damages to normal gingival epithelioid cells) and patients undergone anti-cancer treatment usually suffer from a low quality of life and even life-threatening complications. This strongly underlines the importance of discovering and developing new and effective treatments to improve the prognosis of oral cancer patients, especially with reduced side effects.

Ginsenosides, the main active ingredients of ginseng, are known to have a variety of pharmacological activities, e.g. antitumor, antifatigue, antiallergic and antioxidant activities. Ginsenosides share a basic structure, composed of gonane steroid nucleus having 17 carbon atoms arranged in four rings. Ginsenosides are metalized in the body, and a number of recent studies suggest that ginsenoside metabolites, rather than naturally occurring ginsenosides, are readily absorbed in the body and act as the active components. Among them, ginsenoside M1 is known as one metabolite of protopanaxadiol-type ginsenosides via the gypenoside pathway by human gut bacteria. Until now, no prior art references report the effect of ginsenoside M1 in treatment of oral cancer.

BRIEF SUMMARY OF THE INVENTION

In the present invention, it is unexpected found that ginsenoside M1 is effective in inhibiting growth, colony formation and migration of oral cancer cells, and reducing tumor growth in oral cancer animals. In particular, it is found that ginsenoside M1 has selective toxicity toward oral cancer cells such that it can be administered in an amount effective in treating oral cancer with less toxic to normal gingival epithelioid cells. Therefore, the present invention provides a new approach for treatment of oral cancer in a subject by administering ginsenoside M1 as an anti-cancer agent and/or cancer metastasis inhibitor, having less side effects.

In particular, the present invention provides a method for treating oral cancer in a subject in need thereof comprising administering to the subject an amount of ginsenoside M1 effective to treat the subject.

Specifically, the method treating of the present invention is effective in inhibiting growth or migration of oral cancer cells. The method treating of the present invention is also effective in reducing tumor growth in a subject with oral cancer.

In some embodiments, the method treating of the present invention comprises administering ginsenoside M1 in an amount selectively toxic to oral cancer cells.

In some embodiments, the oral cancer cells are oral squamous cell carcinoma (OSCC).

In some embodiments, ginsenoside M1 is administered by parenteral or enteral route.

The present invention also provides use of ginsenoside M1 in manufacturing a medicament for treatment of oral cancer in a subject in need. The present invention further provides a composition comprising ginsenoside M1 for use in treating oral cancer in a subject in need.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown In the drawings:

DMSO). (FIG. 3A) The apoptotic DNA breaks was assayed by terminal deoxynucleotidyl transferase dUTP nick end labeling (TUNEL) assay using flow cytometry. (FIG. 3B) The cell cycle distribution was determined by PI staining using flow cytometry. (FIG. 3C) The apoptosis level was measured by PI/Annexin V double staining assay using flow cytometry. (FIG. 3D) The activation levels of caspase-9 and caspase-3 were measured by detecting the degradation of pro-caspase-9 and pro-caspase-3 using Western blotting. The flow cytometry and Western blotting results are representative of three different experiments and the histogram shows the quantification expressed as the mean±SD for these three experiments.  and * indicate a significant difference at the level of $p<0.01$ and $p<0.001$, respectively, compared to vehicle-control cells. (One-way ANOVA with Dunnett's multiple comparisons test).

(FIG. 6A) The tumor volume was determined by measurement of the length (L) and width (W) of the tumor and calculated as tumor volume $(mm3)=(L \times W^2)/2$. (FIG. 6B) The tumor weight was measured after the mice were scarified. (FIG. 6C) The body weight of mice was recorded. The data were expressed as mean±SD; n=6.  and * indicate a significant difference at the level of $p<0.01$ and $p<0.001$, respectively, compared to vehicle-control mice. (One-way ANOVA with Dunnett's multiple comparisons test).

(FIG. 7A) The tumor volume was determined by measurement of the length (L) and width (W) of the tumor and calculated as tumor volume $(mm3)=(L \times W^2)/2$. (FIG. 7B) The tumor weight was measured after the mice were scarified. (FIG. 7C) The body weight of mice was recorded. The data were expressed as mean±SD; n=6. ** indicates a significant difference at the level of $p<0.01$, compared to vehicle-control mice. (One-way ANOVA with Dunnett's multiple comparisons test).

DETAILED DESCRIPTION OF THE INVENTION

Figure 1A:
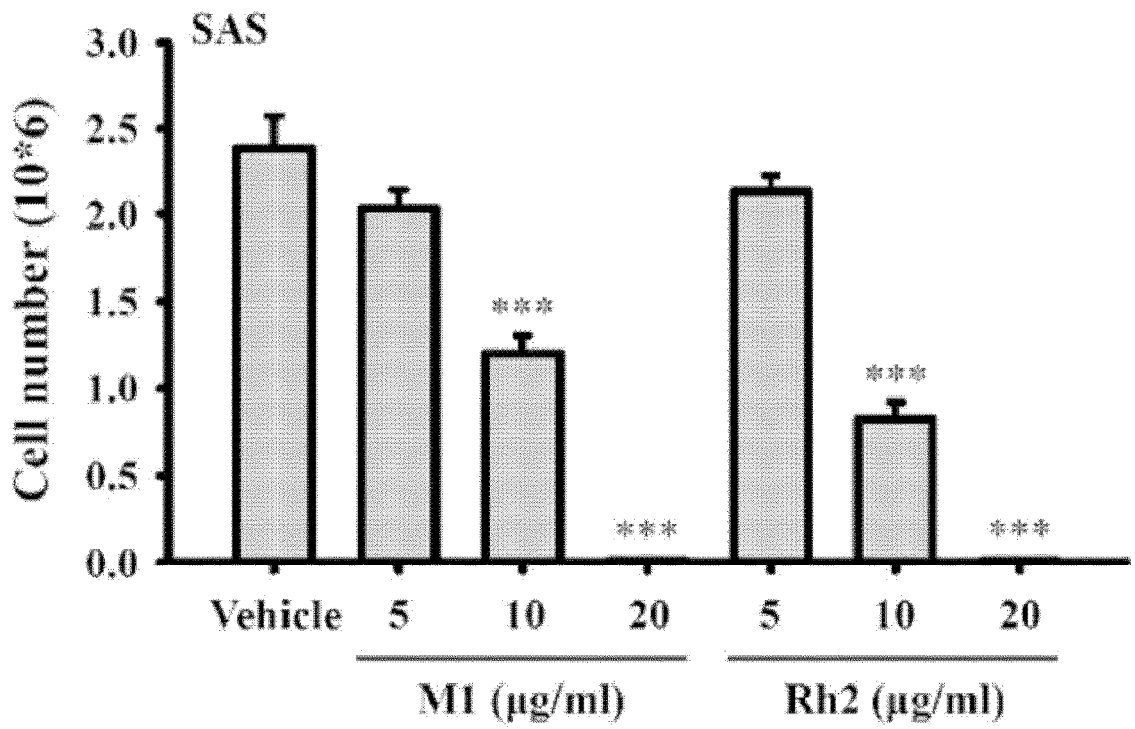
FIGS. 1A-1B show that ginsenoside M1 inhibited the viability of human oral cancer cells. Human oral cancer cell line SAS cells (FIG. 1A) or OECM-1 cells (FIG. 1B) were incubated for 24 h with ginsenoside M1 (5~20 µg/ml), ginsenoside Rh2 (5~20 µg/ml) or vehicle (0.1% DMSO). The live cell numbers were counted by Trypan blue exclusion method. The data were expressed as mean±SD; n=3. *,  and * indicate a significant difference at the level of $p<0.05$, $p<0.01$ and $p<0.001$, respectively, compared to vehicle-control cells. (One-way ANOVA with Dunnett's multiple comparisons test).

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

Apoptosis is one of the important mechanisms of anti-cancer drug-mediated cell death. It is induced by two major pathways: mitochondrial (intrinsic) pathway and death receptor (extrinsic) pathway. Mitochondrial pathway is activated by the release of proapoptotic factors, such as cytochrome c and apoptotic inducing factor, from the mitochondria into the cytosol. The mitochondrial outer membrane permeability is regulated by the Bcl-2 family proteins, which are the central regulator of cytochrome c release and caspases activation (Martinou and Youle, 2011). After being released from the mitochondria, cytochrome c can bind to dATP and apoptotic protease-activating factor-1 which results in the activation of caspase-9 and caspase-3. Activated caspase-3 cleaves various substrates, including poly (ADP-ribose) polymerase (PARP), a DNA repair enzyme, thus leading to inevitable cell death (Green and Reed, 1998). Death receptor pathway involves the Fas and other members of the tumor-necrosis factor receptor family that triggers caspase-8 activation (Thorburn, 2004). Caspase-8 directly activates caspase-3 and cleaves Bid, which then triggers the mitochondrial pathway (Yin, 2000). Reactive oxygen species (ROS) generation has usually been observed during the process of apoptosis in cells subjected to anticancer drugs treatment (Meshkini and Yazdanparast, 2012). Increased ROS level might lead to DNA damage and these damaged cells subsequently undergo either cell cycle arrest to facilitate DNA repair, or induce apoptosis to eliminate the excessively damaged cells (Norbury and Zhivotovsky, 2004). DNA damage might activate p53-dependent apoptosis through inhibiting both the G1/S and the G2/M transitions by directly stimulating the expression of p21WAF1/CIP1, an inhibitor of cyclin-dependent kinases (Cdks) (Vousden and Lu, 2002). DNA damage might also activate protein kinases ATM and ATR which subsequently triggers the activation of the protein kinases Chk1 and Chk2, which in turn inhibits Cdc2 by inactivating Cdc25, the phosphatase that normally activates Cdc2 (Canton and Scott, 2010).

In the present invention, it is unexpectedly found that ginsenoside M1 can inhibit growth and migration of oral cancer cells. It is also demonstrated in this present invention that ginsenoside M1 is effective in reducing tumor growth in an animal model with oral cancer. Specifically, ginsenoside M1 is effective in inhibiting the viability and colony formation while inducing apoptosis, and reducing migration activity, of oral cancer cells. These results indicate that ginsenoside M1 can prevent and mitigate oral cancer. More specifically, ginsenoside M1 has selective toxicity toward oral cancer cells such that it can be administered in an amount effective in killing oral cancer cells with less toxic to normal cells e.g. normal gingival epithelioid cells.

Therefore, the present invention provides a method for treating oral cancer in a subject in need thereof comprising administering to the subject an amount of ginsenoside M1 effective to treat the subject. The present invention also provides use of ginsenoside M1 in manufacturing a medicament for treatment of oral cancer in a subject in need. The present invention further provides a composition comprising ginsenoside M1 for use in treating oral cancer in a subject in need.

In some embodiments, the method of treating is effective in inhibiting growth of oral cancer cells. Specifically, the method of treating is effective in inhibiting the viability and colony formation and/or inducing apoptosis of oral cancer cells.

In some embodiments, the method of treating is effective in inhibiting migration of oral cancer cells.

Ginsenoside M1, 20-O-β-D-glucopyranosyl-20(S)-protopanaxadiol, is one of saponin metabolites known in the art. The chemical structure of ginsenoside M1 is as follows:

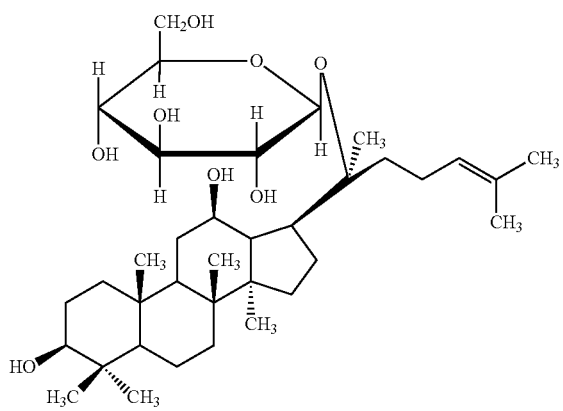

Ginsenoside M1 is known as one metabolite of protopanaxadiol-type ginsenosides via the gypenoside pathway by human gut bacteria. Ginsenoside M1 can be found in blood or urine after intake. Ginsenoside M1 may be prepared from ginseng plants through fungi fermentation by methods known in the art, such as Taiwan Patent Application No. 094116005 (1280982) and U.S. Pat. No. 7,932,057, the entire content of which is incorporated herein by reference. In certain embodiments, the ginseng plants for preparing the ginsenoside M1 include Araliaceae family, *Panax* genus, e.g. *P. ginseng* and *P. pseudo-ginseng* (also named Sanqi). In general, the method of preparation of ginsenoside M1 includes the steps of (a) providing powder of ginseng plant materials (e.g. leaves or stems); (b) providing a fungus for fermenting the ginseng plant materials, wherein the fermentation temperature is ranged from 20-50° C., the fermentation humidity is ranged from 70-100%, the pH value is ranged from 4.0-6.0, and the fermentation period is ranged from 5-15 days; (c) extracting and collecting the fermentation products; and (d) isolating 20-O-β-D-glucopyranosyl-20(S)-protopanaxadiol from the fermentation products.

When ginsenoside M1 is described as "isolated" or "purified" in the present invention, it should be understood as not absolutely isolated or purified, but relatively isolated or purified. For example, purified ginsenoside M1 refers to one that is more purified compared to its naturally existing form. In one embodiment, a preparation comprising purified ginsenoside M1 may comprise ginsenoside M1 in an amount of more than 50%, more than 60%, more than 70%, more than 80%, more than 90%, or 100% (w/w) of the total preparation. It should be understood that when a certain number was used herein to show a ratio or dosage, said number generally includes that within the range of 10% more and less, or more specifically, the scope of 5% more and less than the number.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom or conditions of the disorder, a progression of the disorder or at risk of developing the disorder, with the purpose to cure, heal, alleviate, relieve, alter, remedy, ameliorate, improve, or affect the disorder, the symptoms or conditions of the disorder, the disabilities induced by the disorder, or the onset or progression of the disorder.

The term "side effects" as used herein refers to adverse effects induced by anti-cancer treatment. Particularly, for oral cancer treatment, the resultant side effects include toxic damages to normal gingival epithelioid cells, for example.

The term "therapeutically effective amount" used herein refers to the amount of an active ingredient to confer a therapeutic effect in a treated subject. For example, an effective amount of the ingredient for treating cancer is an amount of such ingredient that can inhibit growth or migration of cancer cells. Specifically, such amount is effective in reducing the number of target cancer cells by at least 10%, e.g. 20%, 30%, 40%, 50%, 60%, 70%, 80%, 90%, or 100%, as compared with the number of target cancer cells without treatment with such ingredient. Preferably, such amount is selectively toxic to target cancer cells. In some embodiments, the ingredient is administered in an amount that selectively provides more toxicity to target cancer cells than to normal cells. For example, in certain examples, the ingredient can be administered in such amount which is effectively in reducing the number of target cancer cells by more than 50% (e.g, 60%, 70%, 80%, 90% or 100%) when compared with the number of target cancer cells without treatment with the ingredient, while causing less toxicity to normal cells e.g. reducing the number of normal cells by less than 50% (e.g. 40%, 30%, 20%, 10%, or less) when compared with the number of normal cells without treatment with the ingredient.

The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of ginsenoside M1 used in the present invention is 10 to 1,000 mg/kg daily. In some examples, the oral the oral dosage of ginsenoside M1 used in the present invention is 100 to 300 mg/kg daily, 50 to 150 mg/kg daily, 25 to 100 mg/kg daily, 10 to 50 mg/kg daily, or 5 to 30 mg/kg daily. In addition, in some embodiments of the invention, ginsenoside M1 is administered periodically for a certain period of time, for example, daily administration for at least 15 days, one month or two months or longer.

According to the present invention, ginsenoside M1 may be used as an active ingredient for treating oral cancer. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, ginsenoside M1 or compositions comprising ginsenoside M1 as the active ingredient may be used in treating individuals with oral cancer or at risk of oral cancer. Specifically, ginsenoside M1 or compositions comprising ginsenoside M1 as the active ingredient may be administered to individuals with oral cancer or individuals at the risk of acquiring oral cancer, in an amount effective in inhibiting growth or migration of oral cancer cells, so as to prevent occurrence of the disease or improve the symptoms or delay deterioration of the symptoms. One certain example of oral cancer is oral squamous cell carcinoma (OSCC). In some preferred embodiments, ginsenoside M1 or compositions comprising ginsenoside M1 according to the present invention is administered in an amount that is selectively toxic to oral cancer cells but less toxic to normal cells.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Ginsenoside M1, 20-O-β-D-glucopyranosyl-20(S)-protopanaxadiol was prepared by methods known in the art, such as those described in Taiwan Patent Application No. 094116005 (1280982) and U.S. Pat. No. 7,932,057.

In the present study, we have investigated the efficacy and associated mechanisms of ginsenoside M1 in vitro and in vivo. We demonstrated that ginsenoside M1 dose-dependently inhibited the viability of human OSCC SAS and OECM-1 cells, with similar efficacy to the ginsenoside Rh2. Notably, ginsenoside M1 showed less toxic to normal human gingival epithelioid cell line SG than ginsenoside Rh2. To gain further insight into the mode of action of ginsenoside M1, four assays targeting hallmarks of apoptosis, namely (1) the apoptotic DNA breaks assayed by terminal deoxynucleotidyl transferase dUTP nick end labeling (TUNEL) assay, (2) the cell cycle assayed by flow cytometry after propidium iodide (PI)-staining nuclei, (3) the PI/Annexin V double staining assay, and (4) caspase activation were performed. We demonstrated that ginsenoside M1 significantly increased apoptotic DNA breaks, G1 phase arrest, PI/Annexin V double positive staining and caspase-3/9 activation in OECM-1 and SAS cells. In addition, we demonstrated that ginsenoside M1 dose-dependently inhibited the colony formation and migration ability of SAS and OECM-1 cells. Furthermore, oral administration or subcutaneous injection of ginsenoside M1 significantly reduced the tumor growth in SAS xenograft mice. These results indicate that ginsenoside M1 can be developed into a potential therapeutic against OSCC.

Example 1: Ginsenoside M1 Inhibited the Viability of Human Oral Cancer Cells

Figure 1B:
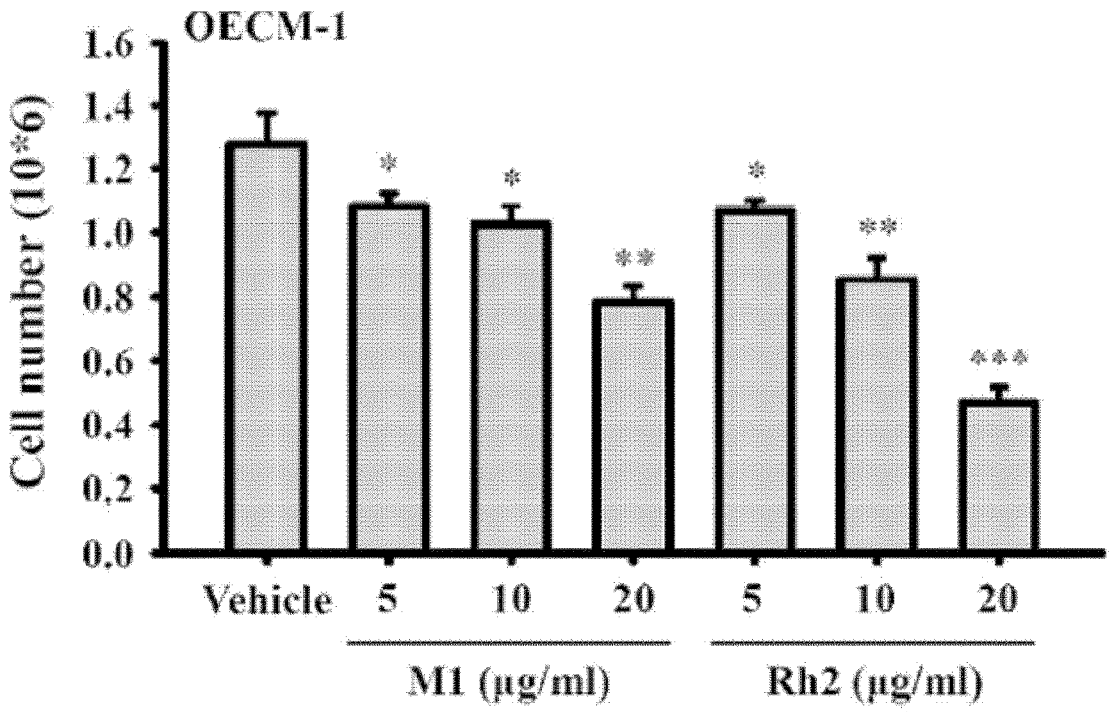

Plate $5 \times 10^5$ human oral cancer cells SAS per 6-cm dish in 2 ml of culture medium and were grown overnight at 37° C. in a 5% $CO_2$ incubator. The cells were incubated for 24 h with ginsenoside M1 (5~20 μg/ml), ginsenoside Rh2 (5~20 μg/ml) or vehicle. Each group contains a final DMSO concentration of 0.1%. Thereafter, the cell numbers were counted by Trypan blue exclusion method. We found that ginsenoside M1 and ginsenoside Rh2 dose-dependently inhibited the cell numbers of human oral cancer SAS cells (FIG. 1A) and human oral cancer OECM-1 cells (FIG. 1B). These results indicated that both ginsenoside M1 and ginsenoside Rh2 inhibited the viability of human oral cancer cells; however, there was no significant difference between ginsenoside M1 and ginsenoside Rh2. The data were expressed as mean±SD; n=3. *,  and * indicate a significant difference at the level of $p<0.05$, $p<0.01$ and $p<0.001$, respectively, compared to vehicle-control cells. (One-way ANOVA with Dunnett's multiple comparisons test).

Example 2: Ginsenoside M1 Showed Less Toxic to Normal Human Gingival Epithelioid Cells than Ginsenoside Rh2

Figure 2:
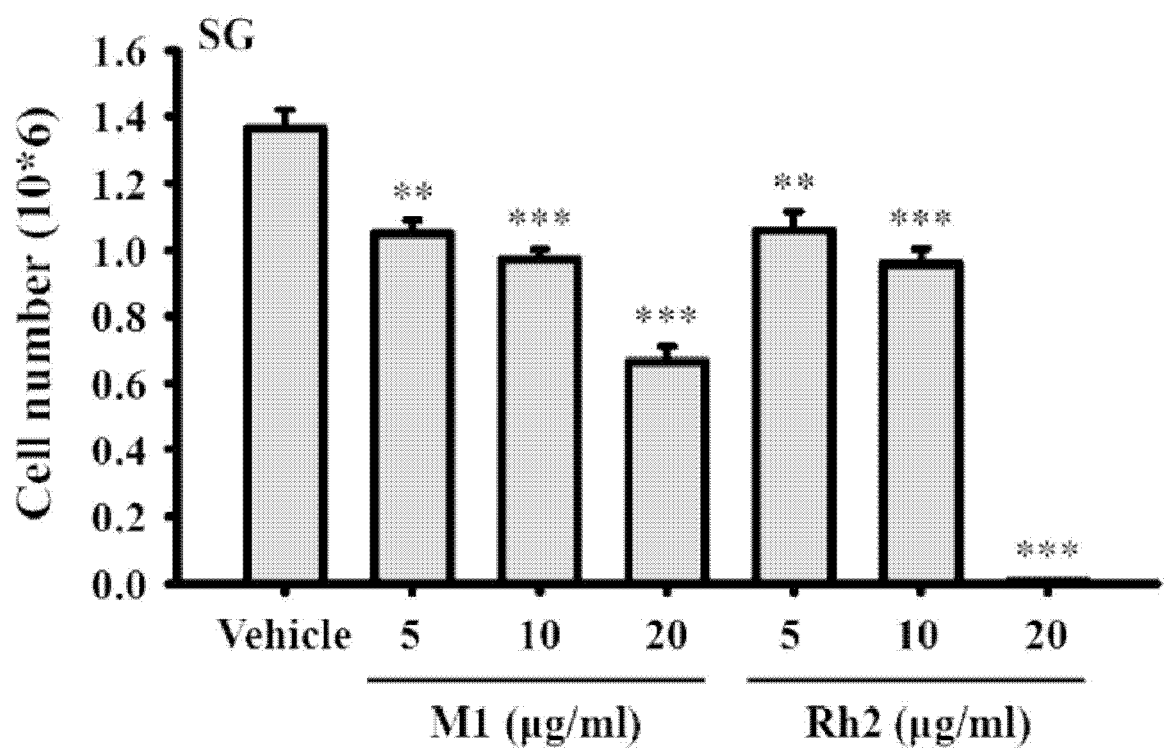
FIG. 2 shows that ginsenoside M1 showed less toxic to normal human gingival epithelioid cells than ginsenoside Rh2. Human normal human gingival epithelioid cell line SG cells were incubated for 24 h with ginsenoside M1 (5~20 µg/ml), ginsenoside Rh2 (5~20 µg/ml) or vehicle (0.1% DMSO). The live cell numbers were counted by Trypan blue exclusion method. The data were expressed as mean±SD; n=3.  and * indicate a significant difference at the level of $p<0.01$ and $p<0.001$, respectively, compared to vehicle-control cells. (One-way ANOVA with Dunnett's multiple comparisons test).

Plate $5 \times 10^5$ normal human gingival epithelioid cell line SG per 6-cm dish in 2 ml of culture medium and were grown overnight at 37° C. in a 5% $CO_2$ incubator. The cells were incubated for 24 h with ginsenoside M1 (5~20 μg/ml), ginsenoside Rh2 (5~20 μg/ml) or vehicle. Each group contains a final DMSO concentration of 0.1%. Thereafter, the cell numbers were counted by Trypan blue exclusion method. We found that ginsenoside M1 showed less toxic to SG cells than ginsenoside Rh2 (FIG. 2). Ginsenoside Rh2 at 20 µg/ml completely killed the SG cells; however, ginsenoside M1 at 20 µg/ml only reduced 50% cell number compared to control cells (namely at least 50% normal cells were preserved) (FIG. 2). The data were expressed as mean±SD; n=3.  and * indicate a significant difference at the level of $p<0.01$ and $p<0.001$, respectively, compared to vehicle-control cells. (One-way ANOVA with Dunnett's multiple comparisons test).

Example 3: Ginsenoside M1 Induced Apoptosis in Human Oral Cancer Cells

Figure 3A:
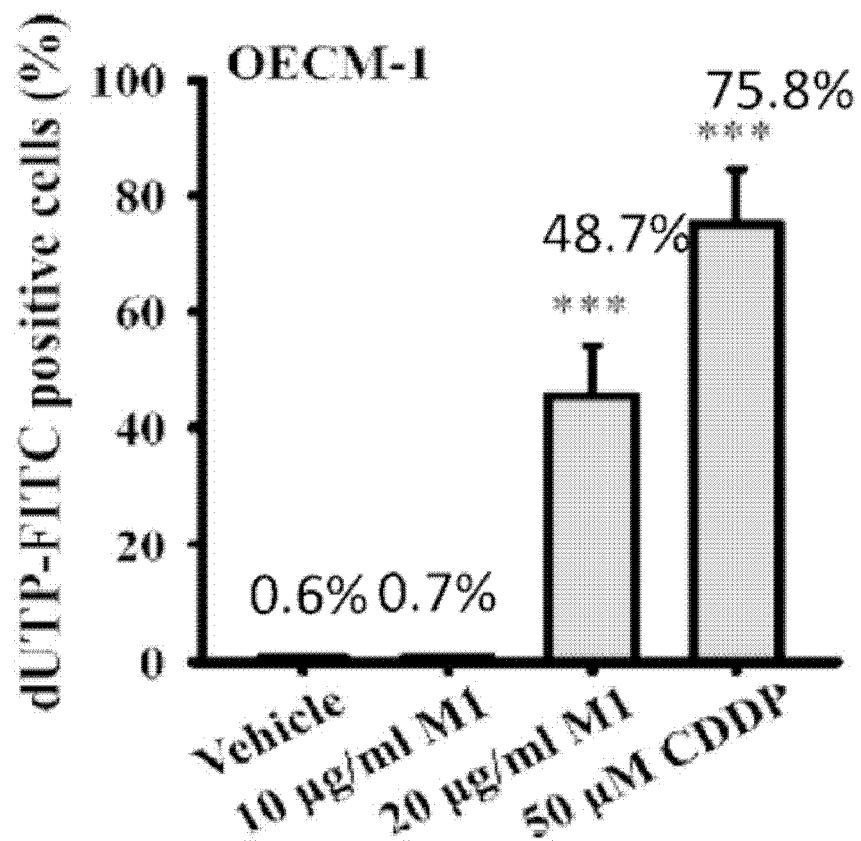
FIGS. 3A-3D show that ginsenoside M1 induced apoptosis in human oral cancer cells. Human oral cancer cell line OECM-1 cells were incubated for 24 h with ginsenoside M1 (10~20 µg/ml), 50 µM cistaplatin (CDDP) or vehicle (0.1%
Figure 3B:
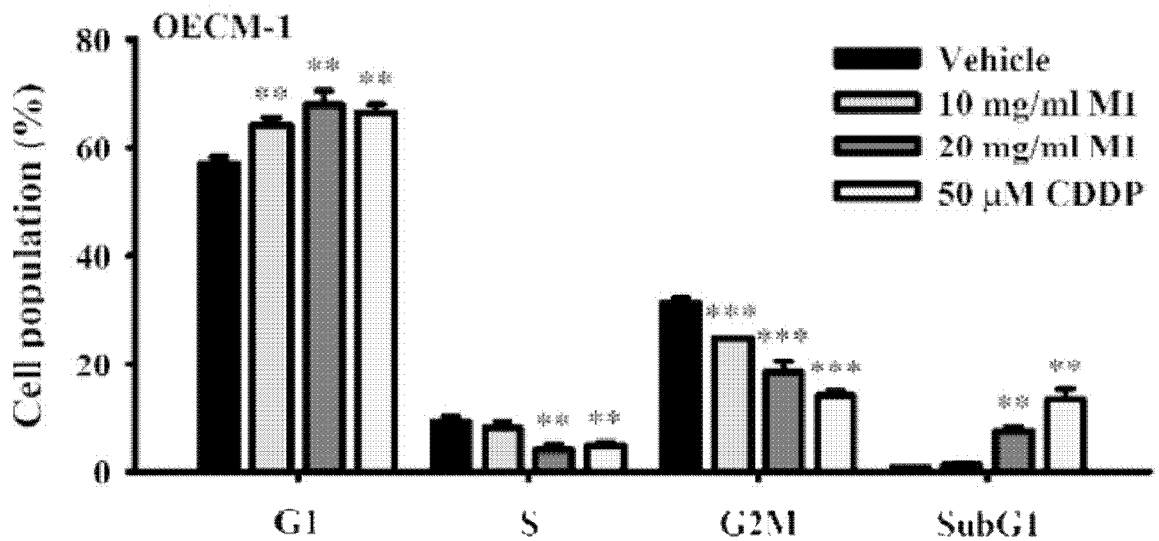
Figure 3C:
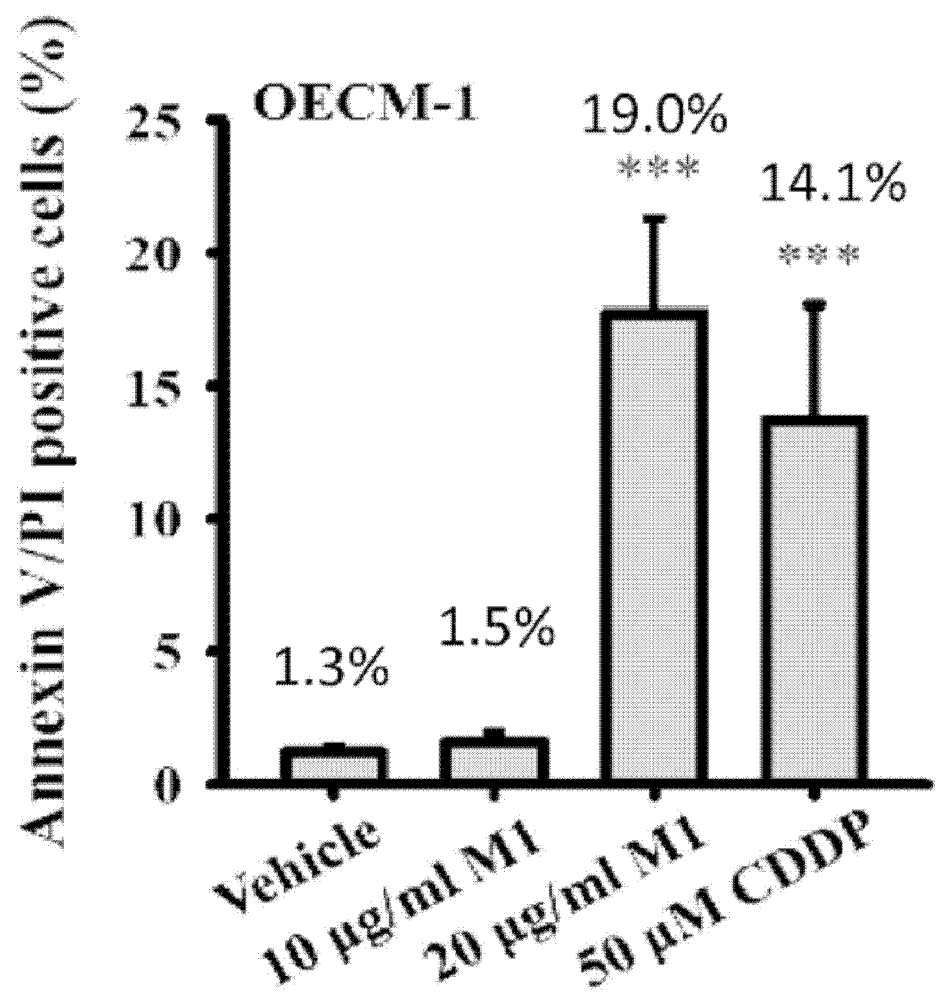
Figure 3D:
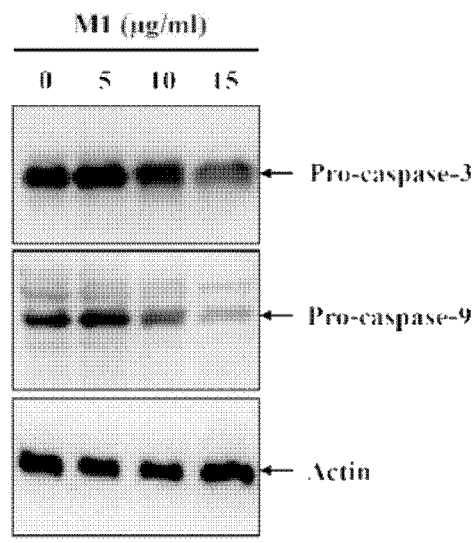
Figure 3D:
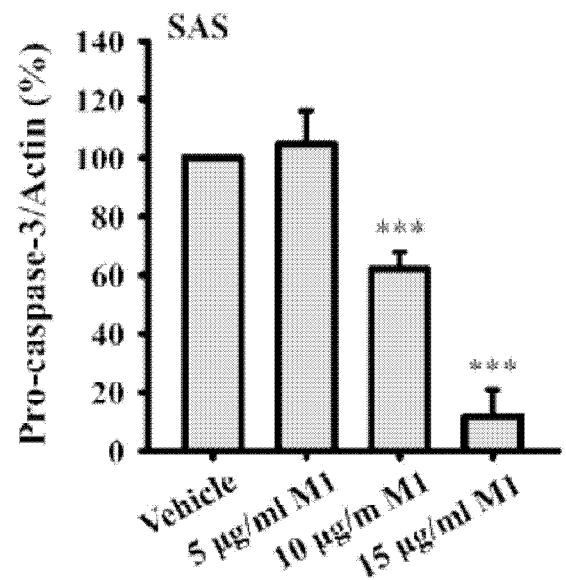
Figure 3D:
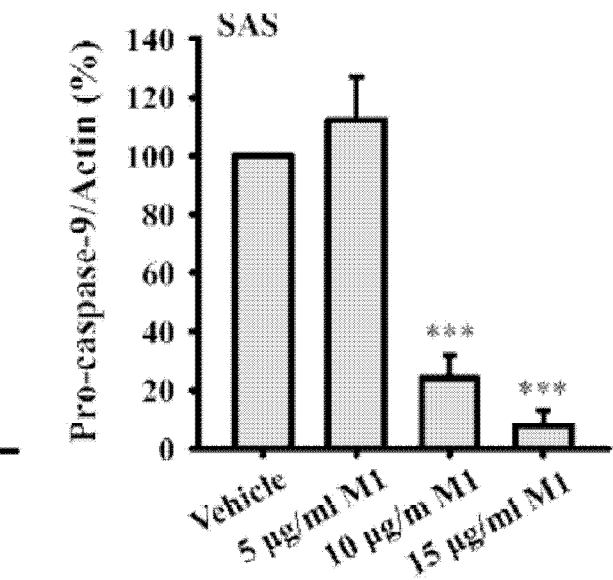

To gain further insight into the mode of action of ginsenoside M1, three assays targeting hallmarks of apoptosis, namely (1) the apoptotic DNA breaks assayed by terminal deoxynucleotidyl transferase dUTP nick end labeling (TUNEL) assay, (2) the cell cycle assayed by flow cytometry after propidium iodide (PI)-staining nuclei, (3) the PI/Annexin V double staining assay, and (4) caspase activation were performed. Plate $1\times10^6$ human oral cancer cells OECM-1 per 6-cm dish in 2 ml of culture medium and were grown overnight at 37° C. in a 5% $CO_2$ incubator. The cells were incubated for 24 h with ginsenoside M1 (10~20 µg/ml), 50 µM cistaplatin (CDDP) or vehicle. Each group contains a final DMSO concentration of 0.1%. Thereafter, three assays were performed. We found that 20 µg/ml ginsenoside M1 and 50 µM CDDP, but not 10 µg/ml ginsenoside M1 significantly induced apoptotic DNA breaks in OECM-1 cells (FIG. 3A). In addition, the effect of ginsenoside M1 on the cell cycle distribution in OECM-1 cells was determined and we found that the cells in G1 phase increased in a concentration-dependent manner after treatment with ginsenoside M1 and CDDP, while concomitantly decreasing the percentage of cells in S and G2/M phase as compared with the control cells, indicating that ginsenoside M1 and CDDP induced cell cycle arrest at G1 phase (FIG. 3B). The cells in sub-G1 phase increased after treatment with ginsenoside M1 and CDDP. (FIG. 3B). Moreover, we found that 20 µg/ml ginsenoside M1 and 50 µM CDDP, but not 10 µg/ml ginsenoside M1 significantly increased the percentage of OECM-1 cells with PI/Annexin V double positive staining (FIG. 3C). These results indicated that ginsenoside M1 induced human oral cancer cells OECM-1 apoptosis significantly at concentration of 20 µg/ml. The apoptosis induction activity of ginsenoside M1 in human oral cancer SAS cells was confirmed as ginsenoside M1 induced a decrease of the precursors of caspase-3 and caspase-9 in a dose-dependent manner, indicating that caspase 3 and caspase 9 were activated by ginsenoside M1 (FIG. 3D). The data were expressed as mean±SD; n=3.  and * indicate a significant difference at the level of $p<0.01$ and $p<0.001$, respectively, compared to vehicle-control cells. (One-way ANOVA with Dunnett's multiple comparisons test).

Figure 4A:
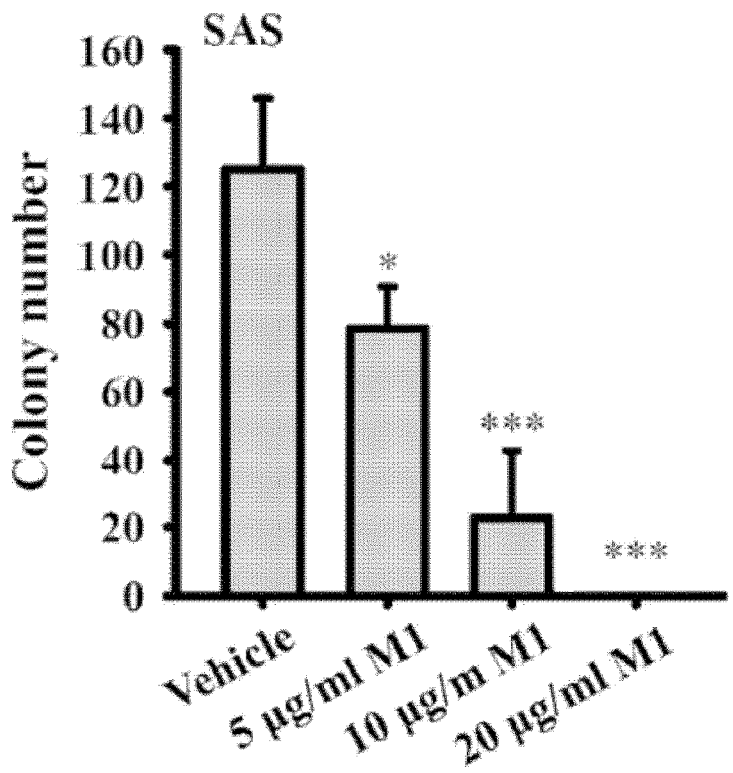
FIGS. 4A-4B show ginsenoside M1 reduced the colony formation ability of human oral cancer cells. Human oral cancer cell line SAS cells (FIG. 4A) or OECM-1 cells (FIG. 4B) were incubated for 10 days with ginsenoside M1 (5~20 μg/ml) or vehicle (0.1% DMSO). The cells were fixed in 4% ice-cold paraformaldehyde and stained with 0.1% crystal violet, and the colonies were counted. The data were expressed as mean±SD; n=4. * and *** indicate a significant difference at the level of $p<0.05$ and $p<0.001$, respectively, compared to vehicle-control cells. (One-way ANOVA with Dunnett's multiple comparisons test).
Figure 4B:
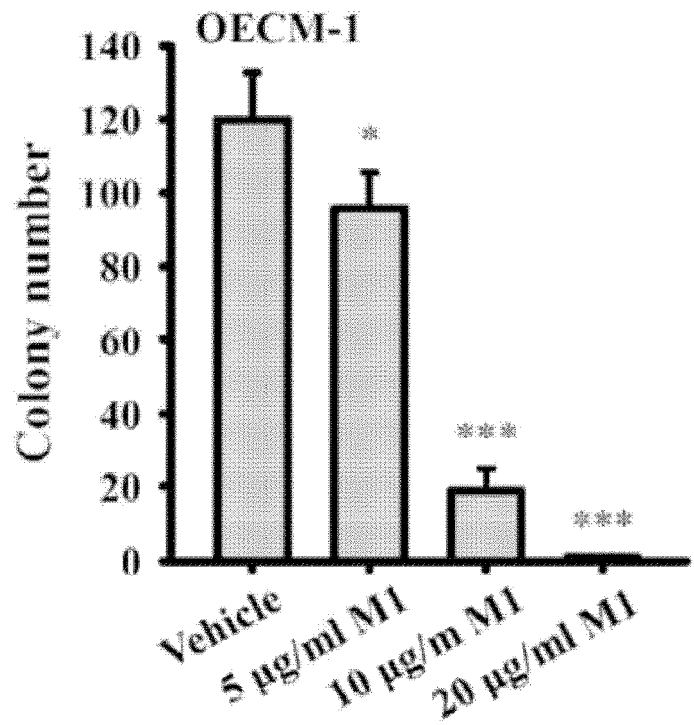

Example 4: Ginsenoside M1 Reduced the Colony Formation Ability of Human Oral Cancer Cells Plate 150 human oral cancer cells SAS or OECM-1 per 6-cm dish in 3 ml of culture medium and were grown overnight at 37° C. in a 5% $CO_2$ incubator. The cells were incubated for 10 days with ginsenoside M1 (5~20 µg/ml) or vehicle. The cells were changed for fresh medium containing the same concentration of ginsenoside M1 at day 5. The cells were fixed in 4% ice-cold paraformaldehyde for 15 min at 37° C., and stained with 0.1% crystal violet 10 min at room temperature. The colonies were counted and we found that ginsenoside M1 dose-dependently inhibited the colony formation ability of SAS cells (FIG. 4A) and OECM-1 cells (FIG. 4B). The data were expressed as mean±SD; n=4. * and *** indicate a significant difference at the level of $p<0.05$ and $p<0.001$, respectively, compared to vehicle-control cells. (One-way ANOVA with Dunnett's multiple comparisons test).

Figure 5A:
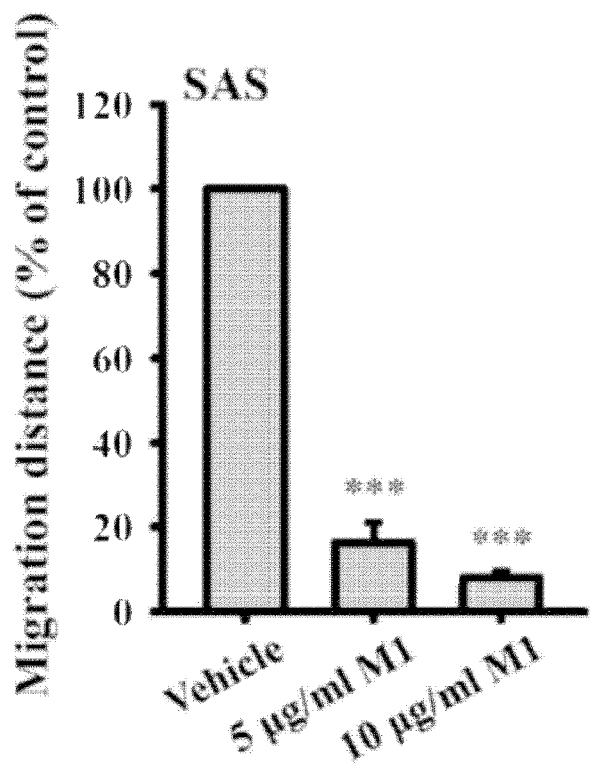
FIGS. 5A-5B show ginsenoside M1 reduced the migration ability of human oral cancer cells. Human oral cancer cell line SAS cells (FIG. 5A) or OECM-1 cells (FIG. 5B) were cultured in 6-cm dish until the cells reached 100% confluence forming a monolayer. A clear zone was created by scratching using a sterile 200-μl pipette tip. The cells were incubated for 24 h (SAS cells) or 18 h (OECM-1 cells) with ginsenoside M1 (5~10 μg/ml) or (0.1% DMSO). The migration distance was measured and compared to the vehicle-control cells. The data were expressed as mean±SD; n=3. *** indicates a significant difference at the level of $p<0.001$, compared to vehicle-control cells. (One-way ANOVA with Dunnett's multiple comparisons test).
Figure 5B:
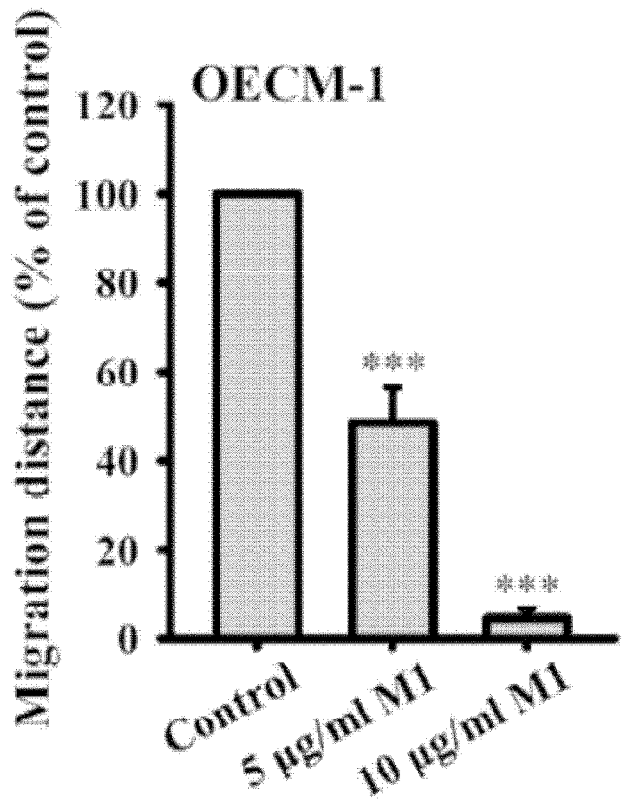

Example 5: Ginsenoside M1 Reduced the Migration Ability of Human Oral Cancer Cells The cell migration ability was measured by wound healing assay. Plate $5\times10^6$ human oral cancer SAS cells or OECM-1 cells per 6-cm dish in 2 ml of culture medium and were grown overnight at 37° C. in a 5% $CO_2$ incubator until the cells reached 100% confluence forming a monolayer. We used a sterile 200-µl pipette tip to create a scratched clear zone on the culture dish, and the wounds photographed by a phase contrast microscope as the baseline. The cells were incubated for 24 h (SAS cells) or 18 h (OECM-1 cells) with ginsenoside M1 (5~10 µg/ml) or vehicle, and then the wounds photographed again. We found that ginsenoside M1 at 5 or 10 µg/ml significantly inhibited the migration ability of human oral cancer cells SAS (FIG. 5A) and OECM-1 cell (FIG. 5B). The data were expressed as mean±SD; n=3. *** indicates a significant difference at the level of $p<0.001$, compared to vehicle-control cells. (One-way ANOVA with Dunnett's multiple comparisons test).

Example 6: Ginsenoside M1 Reduced Human Oral Cancer Growth in Mice

Figure 6A:
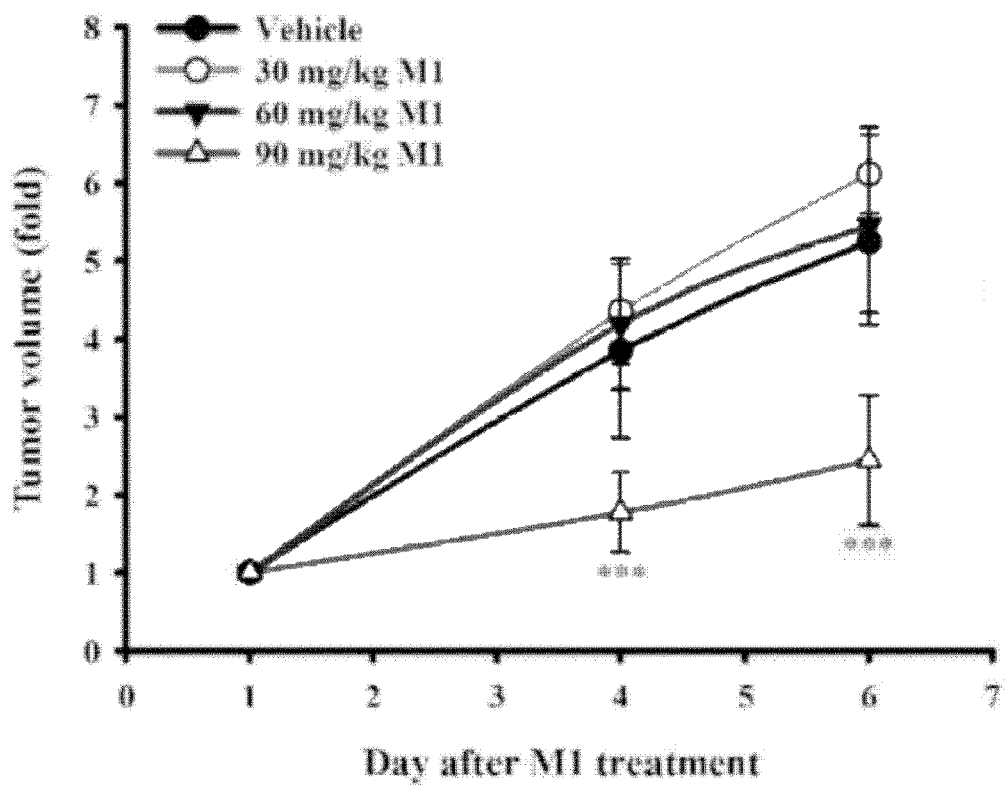
FIGS. 6A-6C show oral administration of ginsenoside M1 reduced human oral cancer growth in mice. Human oral cancer cell line SAS cells Xenografts mice with tumor size around 40~60 $mm^3$ were given a daily oral administration of either ginsenoside M1 (30-90 mg/kg) or vehicle for 5 successive days.
Figure 6B:
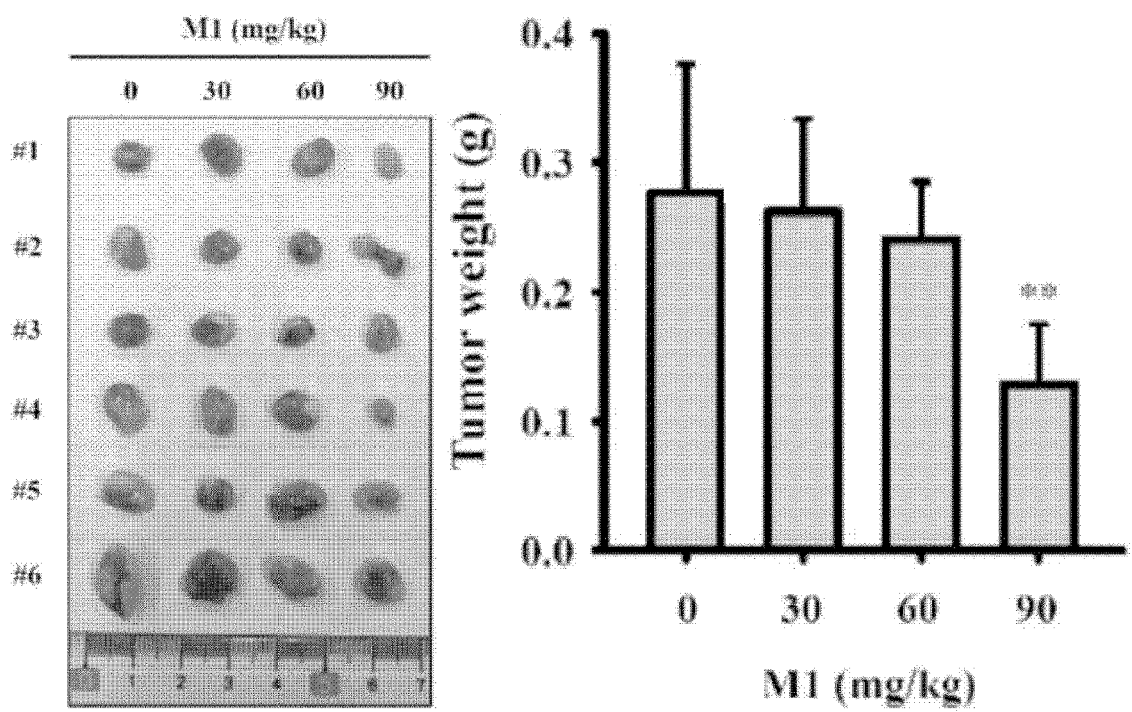
Figure 6C:
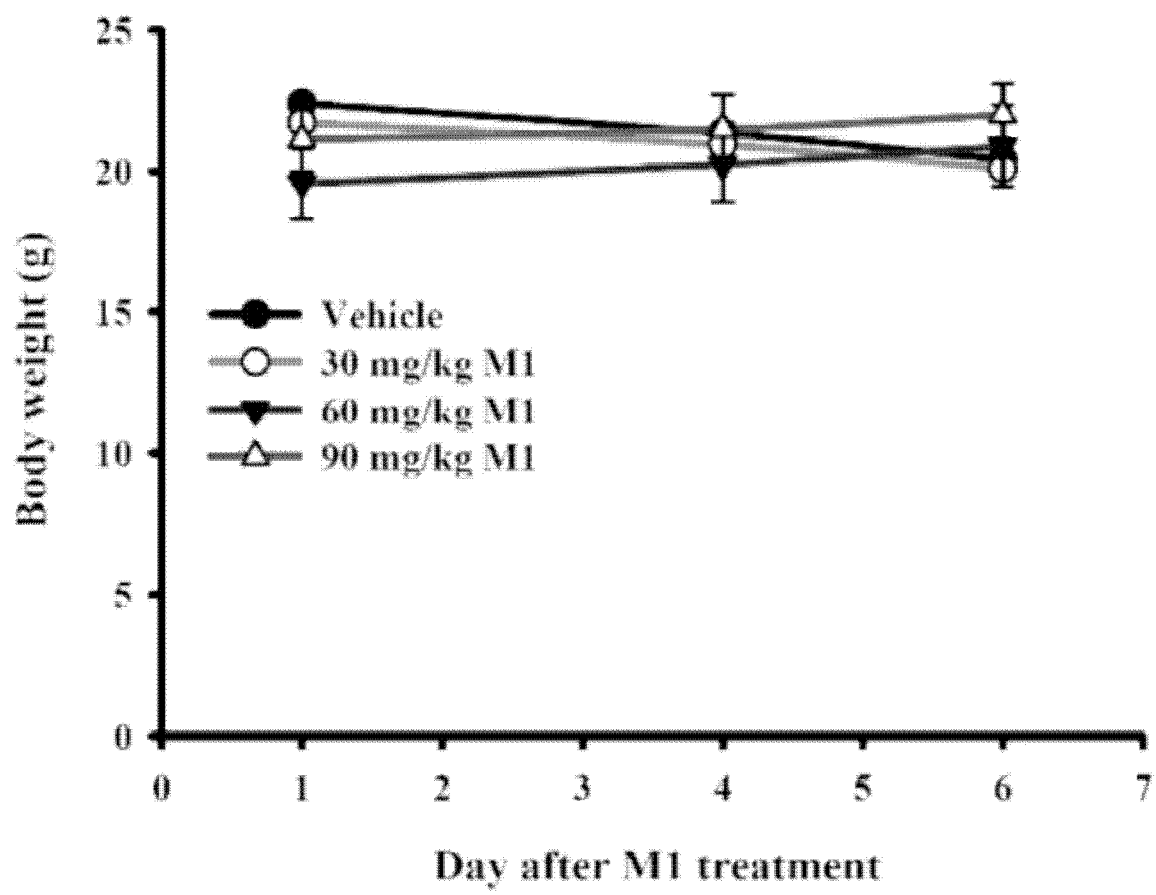

To evaluate the anti-cancer activity of ginsenoside M1 in vivo, human oral cancer xenografts were used. Six-week-old male congenital athymic BALB/c nude (nu/nu) mice were purchased from BioLASCO Taiwan Co., Ltd (Ilan, Taiwan), and housed in a room under controlled temperature (23±3° C.) and relative humidity (50±5%). Animal experiments were performed with the approval of the Institutional Animal Care and Use Committee of the National Ilan University (approval number: No. 106-13) according to the NIH Guide for the Care and Use of Laboratory Animals. Xenografts mice were established by subcutaneous (SC) injection of $2\times10^6$ human oral cancer cells SAS (in 75 µl PBS+75 µl Matrigel) on the backs of the nude mice. After the tumor has reached about 40~60 mm³ in size, the mice were randomized into six groups (six mice each): (1) oral vehicle control; (2) oral 30 mg/kg ginsenoside M1; (3) oral 60 mg/kg ginsenoside M1; (4) oral 90 mg/kg ginsenoside M1; (5) SC vehicle control; (6) SC 20 mg/kg ginsenoside M1. The mice were given a daily oral administration or SC injection of either vehicle or ginsenoside M1 for 5 successive days. The mice were scarified at 24 h after received the last dose of ginsenoside M1 or vehicle. The tumor volume (TV) was determined by measurement of the length (L) and width (W) of the tumor. The TV on day n (TVn) was calculated as TV (mm3)=$(L\times W^2)/2$. The relative tumor volume on day n (RTVn) versus day 0 was expressed according to the following formula: RTVn=TVn/TV0. We found that oral administration of ginsenoside M1 at 90 mg/kg significantly reduced the tumor size compared to vehicle control group; however, oral administration of ginsenoside M1 at 30 and 60 mg/kg did not significant reduce the tumor size (FIG. 6A) and tumor weight (FIG. 6B). Oral administration of ginsenoside M1 did not significantly affect the body weight of mice (FIG. 6C). The data were expressed as mean±SD; n=6.  and * indicate a significant difference at the level of p<0.01 and p<0.001, respectively, compared to vehicle-control mice. (One-way ANOVA with Dunnett's multiple comparisons test).

Figure 7A:
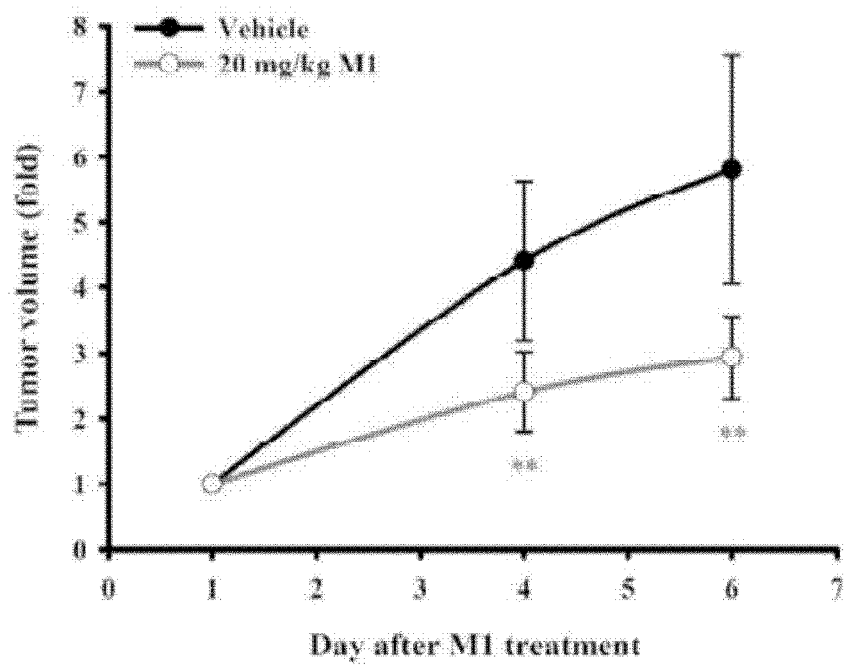
FIGS. 7A-7C show subcutaneous (SC) injection of ginsenoside M1 reduced human oral cancer growth in mice. Human oral cancer cell line SAS cells Xenografts mice with tumor size around 40~60 $mm^3$ were given a daily SC injection of either ginsenoside M1 (20 mg/kg) or vehicle for 5 successive days.
Figure 7B:
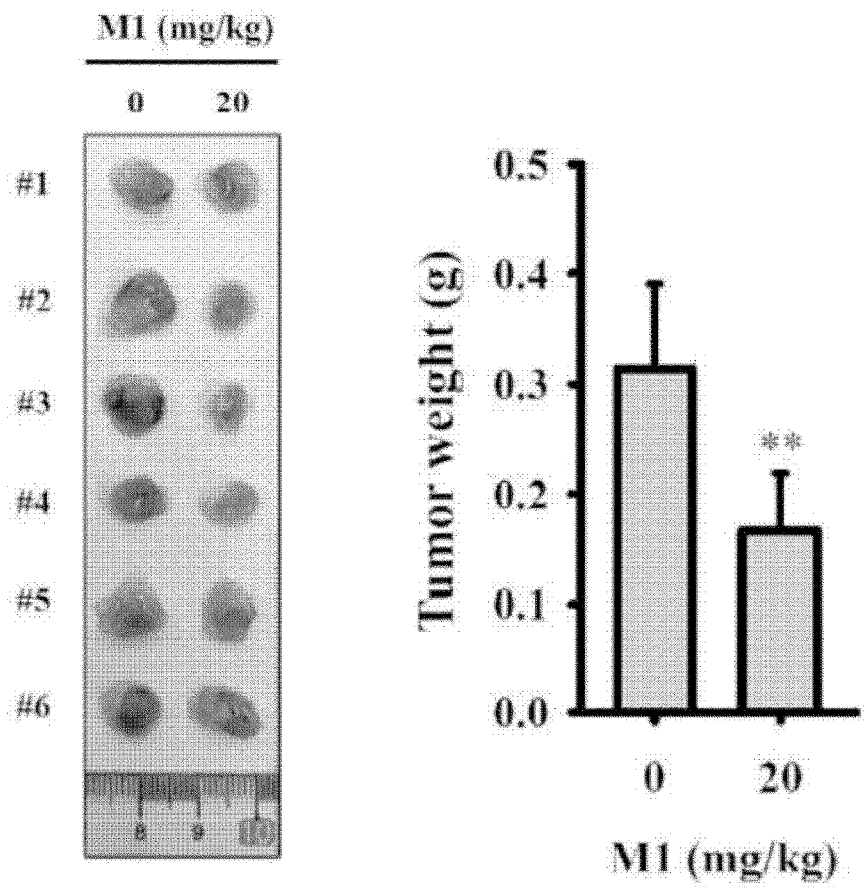
Figure 7C:
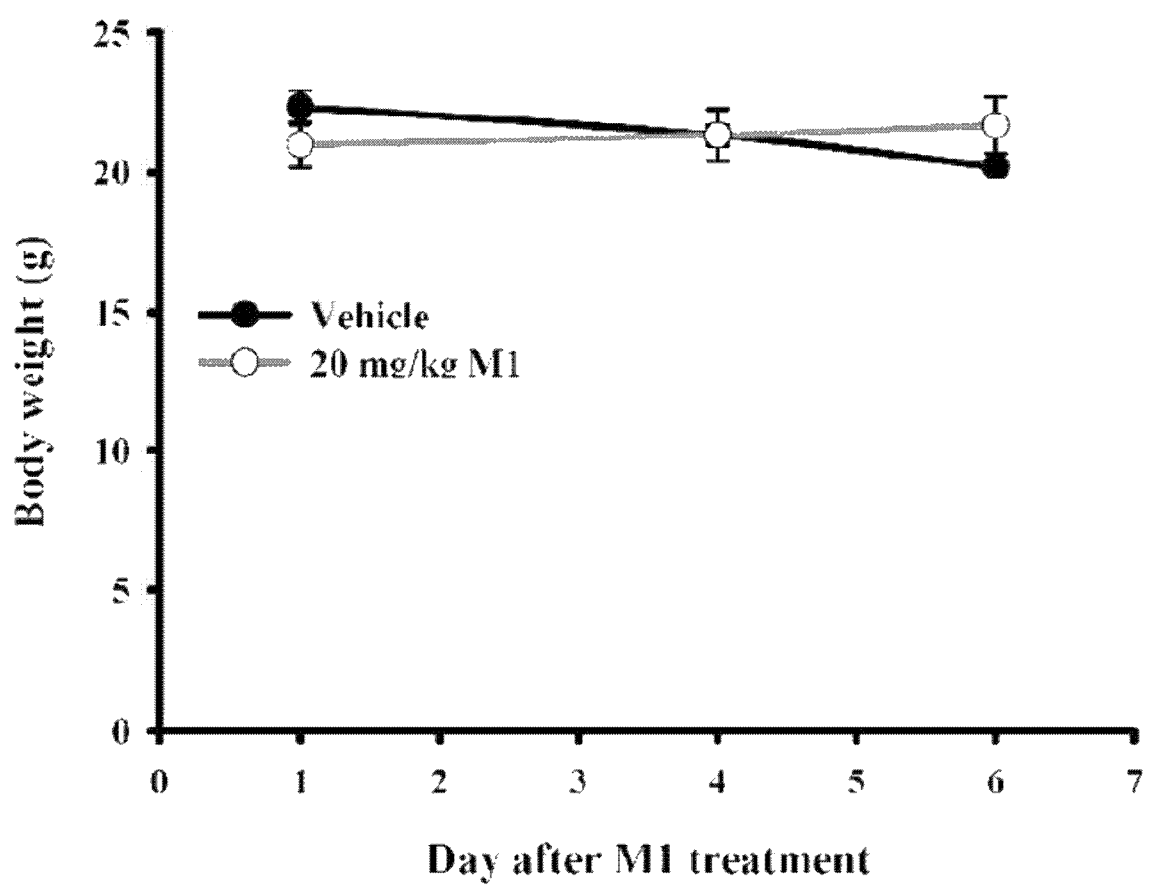

In addition, SC injection of 20 mg/kg ginsenoside M1 also significantly reduced the tumor size (FIG. 7A) and tumor weight (FIG. 7B) compared to vehicle control group. SC injection of ginsenoside M1 did not significantly affect the body weight of mice (FIG. 7C). The data were expressed as mean±SD; n=6. ** indicates a significant difference at the level of p<0.01, compared to vehicle-control mice. (One-way ANOVA with Dunnett's multiple comparisons test).

REFERENCES

Canton D A, Scott J D. (2010) Chk-ing in and Chk-ing out: kinase compartmentalization comes to checkpoint control. Mol Cell 40: 1-2.
Green D R, Reed J C. (1998) Mitochondria and apoptosis. Science 281: 1309-1312.
Martinou J C, Youle R J. (2011) Mitochondria in apoptosis: Bcl-2 family members and mitochondrial dynamics. Dev Cell 21: 92-101.
Meshkini A, Yazdanparast R. (2012) Involvement of oxidative stress in taxol-induced apoptosis in chronic myelogenous leukemia K562 cells. Exp Toxicol Pathol 64: 357-365.
Murugan A K, Munirajan A K, Tsuchida N. (2012) Ras oncogenes in oral cancer: the past 20 years. Oral Oncol 48: 383-392.
Norbury C J, Zhivotovsky B. (2004) DNA damage-induced apoptosis. Oncogene 23: 2797-2808.
Petti S, Scully C. (2007) Oral cancer knowledge and awareness: primary and secondary effects of an information leaflet. Oral Oncol 3: 408-415.
Thorburn A. (2004) Death receptor-induced cell killing. Cellular Signalling 16: 139-144.
Tsantoulis P K, Kastrinakis N G, Tourvas A D, Laskaris G, Gorgoulis V G. (2007) Advances in the biology of oral cancer. Oral Onc. 43: 523-534.
Vousden K H, Lu X. (2002) Live or let die: the cell's response to p53. Nat Rev Cancer 2: 594-604.
Yin X M. (2000) Signal transduction mediated by Bid, a pro-death Bcl-2 family proteins, connects the death receptor and mitochondria apoptosis pathways. Cell Research 10: 161-167.

We claim:

1. A method of treating oral cancer in a subject in need thereof comprising
administering to the subject an amount of ginsenoside M1 effective to treat the subject, wherein ginsenoside M1 is administered in an amount selectively toxic to oral cancer cells.
2. The method of claim 1, wherein the method of treating is effective in inhibiting growth or migration of oral cancer cells.
3. The method of claim 2, wherein ginsenoside M1 is administered in an amount causing reduction of the number of normal cells by less than 50% when compared with the number of normal cells without treatment with ginsenoside M1.
4. The method of claim 2, wherein the oral cancer cells are oral squamous cell carcinoma (OSCC) cells.
5. The method of claim 1, wherein the ginsenoside M1 is administered by parenteral or enteral route.

* * * * *